US006953535B2

(12) United States Patent
Hecht et al.

(10) Patent No.: US 6,953,535 B2
(45) Date of Patent: Oct. 11, 2005

(54) INITIATOR SYSTEM FOR ACID DENTAL FORMULATIONS

(75) Inventors: Reinhold Hecht, Kaufering (DE); Manfred Ludsteck, Geretsried (DE)

(73) Assignee: 3M Espe Ag, Seefeld (DE)

( * ) Notice: Subject to any disclaimer, the term of this patent is extended or adjusted under 35 U.S.C. 154(b) by 11 days.

(21) Appl. No.: 10/477,723

(22) PCT Filed: May 13, 2002

(86) PCT No.: PCT/EP02/05219

§ 371 (c)(1),
(2), (4) Date: Nov. 14, 2003

(87) PCT Pub. No.: WO02/092023

PCT Pub. Date: Nov. 21, 2002

(65) Prior Publication Data

US 2004/0097613 A1 May 20, 2004

(30) Foreign Application Priority Data

May 16, 2001 (DE) ........................................ 101 24 029

(51) Int. Cl.$^7$ ............................. C09K 3/00; A61F 2/00; C08K 3/10; C08L 41/00; A61K 6/083
(52) U.S. Cl. ............................ 252/183.13; 252/183.12; 252/183.11; 252/182.17; 252/182.23; 252/182.34; 252/188.2; 252/188.1; 252/186.43; 524/556; 524/560; 524/100; 524/781; 524/832; 523/118; 523/115; 526/204
(58) Field of Search ...................... 252/183.13, 183.12, 252/183.11, 182.17, 182.23, 182.34, 188.2, 188.1, 186.43; 524/556, 560, 100, 781, 832; 523/118, 115; 526/204

(56) References Cited

U.S. PATENT DOCUMENTS

| 3,347,954 | A | | 10/1967 | Bredereck et al. |
| 3,541,068 | A | | 11/1970 | Taylor |
| 4,095,018 | A | | 6/1978 | Schmitt et al. |
| 5,095,045 | A | | 3/1992 | Winkel et al. |
| 5,154,762 | A | | 10/1992 | Mitra et al. |
| 5,252,629 | A | | 10/1993 | Imai et al. |
| 5,290,172 | A | * | 3/1994 | Sakuma et al. .............. 433/215 |
| 5,583,164 | A | | 12/1996 | Jochum et al. |
| 5,587,406 | A | * | 12/1996 | Yamamoto et al. ......... 523/116 |
| 5,670,559 | A | * | 9/1997 | Zeng et al. .................. 523/118 |
| 5,688,883 | A | | 11/1997 | Klee et al. |
| 5,968,998 | A | | 10/1999 | Jochum et al. |
| 6,288,138 | B1 | | 9/2001 | Yamamoto et al. |
| 2004/0110864 | A1 | * | 6/2004 | Hecht et al. ................. 523/113 |

FOREIGN PATENT DOCUMENTS

| DE | 1 495 520 | 4/1969 |
| DE | 26 58 538 A1 | 6/1977 |
| DE | 42 19 700 A1 | 12/1992 |
| DE | 197 57 277 A1 | 6/1999 |
| DE | 199 28 238 A1 | 12/2000 |
| EP | 0 047 097 A2 | 3/1982 |
| EP | 0 132 959 A2 | 2/1985 |
| EP | 0 047 097 B1 | 5/1986 |
| EP | 0 132 959 B1 | 12/1987 |
| EP | 0 374 824 A2 | 6/1990 |
| EP | 0 374 824 A3 | 6/1990 |
| EP | 0 410 199 A3 | 1/1991 |
| EP | 0 410 199 A2 | 1/1991 |
| EP | 0 480 785 A2 | 4/1992 |
| EP | 0 480 785 A3 | 4/1992 |
| EP | 0 410 199 B1 | 5/1995 |
| EP | 0 588 878 B1 | 10/1996 |
| EP | 0 480 785 B1 | 12/1996 |
| EP | 0 923 924 A3 | 6/1999 |
| EP | 0 923 924 A2 | 6/1999 |
| WO | WO 92/21314 A1 | 12/1992 |

OTHER PUBLICATIONS

E. Andrzejewska et al., "The role of oxygen in camphorquinone–initiated photopolymerization," Macromol. Chem. Phys., vol. 199, No. 3, Title page, Publication page, Table of Contents, and pp. 441–449 (13 pgs total) (1998).
International Standard, ISO 4049, "Dentistry—Polymer–based filling, restorative and luting materials," Title page, Publication page, Table of Contents, Forward page, Introduction page, and pp. 1–27 (34 pp. total) (Jul. 15, 2000).
Andrzejewska et al., "The role of oxygen in camphorquinone–initiated photopolymerization," Macromol. Chem. Phys., 1999:441–449 (1998).
Bredebeck et al., "Aus dem Institut fur Organische Chemie der Technischen Hochschule Stuttgart Über CH–aktive Polymerisationsinitiatoren* XIII. Mitt. Polymerisationen und Polymerisationsinitiatoren $^{1*}$," Die Mackromolekulare Chemie, 92:70–90, Title page, Publication page, and Table of Contents (26 pgs total) (1966). (Translation in English, "From the Institute of Organic Chemistry of the Technische Universtat Stuttgart About CH–Active Polymerization Initiators* XIII. Information about polymerizations and polymerization initiators[1*]," Marcomolecular Chemistry, 92:70–90, Title page, and Table of Contents (20 pgs total) (1966)).

(Continued)

Primary Examiner—Joseph D. Anthony
(74) Attorney, Agent, or Firm—Mueting, Raasch, & Gebhart, P.A.

(57) ABSTRACT

The invention relates to a redox initiator system which allows dental formulations to be cured in acidic medium by way of a free-radical polymerization and which ensures a high level of adhesion of the polymerizing composition to the hard substances of the teeth, namely enamel and, in particular, dentine.

The redox initiator system comprises the following constituents:
(A) from 14.9 to 50% by weight of a barbituric acid or thiobarbituric acid and/or of a barbituric or thiobarbituric acid derivative,
(B) from 30 to 75% by weight of a peroxodisulfate compound and/or peroxodiphosphate compound,
(C) from 10 to 35% by weight of a sulfinic acid compound, and
(D) from 0.1 to 5% by weight of a copper compound.

11 Claims, No Drawings

OTHER PUBLICATIONS

Ebel, "2.2.3 pH–Wert–Potentiometrische Methode," Kommentar zur PH. Eur., pp. (10 Lfg. 1999) (6 pgs total) (1997). (Translation in English, "2.2.3 pH–Value–Potentiometric Method," (11 pgs)).

Guertsen et al., *Klinik der Kompositfullung*, Hanser/Gardner Publications, Inc., Cincinnati, U.S., Title page, Publication page, and Table of Contents (4 pgs total) (1989). (Translation in English, "Clinic of Composite Fillings," (3 pgs total)).

Hecht, "6. Basler Werkstoffkunde Symposium," (English translation: "$6^{th}$ Materials Science Symposium of Basel"), 25 pgs. (English translation is 9 pgs.) (Dec. 5–6, 2003).

Hecht et al., "RelyX Unicem FIRST self–adhesive universal resin cement Scientific and Chemical Background Information," Austin, Texas, 67 pgs. (Mar. 2003).

Hecht et al., "Self–adhesion From a One Step to a –Zero Step" Bond Vision or Reality, Presentation at the Norwegian Dental Association, Oslo, Norway, 23 pgs. (Oct. 9, 2003).

* cited by examiner

INITIATOR SYSTEM FOR ACID DENTAL FORMULATIONS

The present application is a U.S. National Stage Application of PCT/EP02/05219, filed 13, May 2002. The application also claims the benefit under 35 U.S.C. §119 of foreign application no. DE 101 24 029.5, filed May 16, 2001.

The present invention relates to a redox initiator system which allows dental formulations to be cured in acidic medium by way of a free-radical polymerization and which ensures a high level of adhesion of the polymerizing composition to the hard substances of the teeth, namely enamel and, in particular, dentine.

Materials based on acrylates and methacrylates are the materials of choice for many dental applications and are known as key constituents of the formulations of bonding materials and composites and also of the compomers and resin-modified glass ionomer cements. These systems are normally cured by way of a free-radical polymerization, with the free radicals being provided via suitable initiator systems photochemically, thermally and/or by redox reactions. The polymerization initiator system has a critical influence on the quality of the dental material.

It is state of the art to cure (meth)acrylate dental materials photochemically. In particular the use of camphorquinone in combination with tertiary amines has been described in numerous applications such as E. Andrzejewska et al., Macromol. Chem. Phys. 199, 441–449 (1998) and EP 0 132 959 A1 or EP 0 047 097 B1.

A further means of initiating a free-radical polymerization lies in the thermal decomposition of suitable starting molecules. For instance, in dentistry, for what are termed hot polymers, use is made of peroxides such as benzoyl peroxide, lauroyl peroxide or tert-butyl perbenzoate and also of further compounds, described for example in EP 0 410 199 A.

The use of initiator systems operating thermally is generally limited to dental products, since the required temperatures are unacceptable for intraoral dentistry applications. For the use of photoinitiators there are also limiting factors. In the cementing of metal restorations with composite-based cements, for example, photoinitiation is not an option. Furthermore, it is not possible to use light to cure layers of arbitrary thickness; i.e., in the filling of deep cavities a bulk filling is not possible and it is necessary to operate using what is called the layer technique (see W. Geurtsen, Klinik der Kompositfüllung, Hanser Verlag Munich, Vienna, 1989).

In order to solve the stated problems systems called redox initiator systems have been proposed in the dental segment. These comprise a combination of a reducing agent with an oxidizing agent, the constituents of the redox system being stored separately for reasons of stability. The resulting systems are therefore paste/paste, powder/liquid or liquid/liquid systems. After these systems have been prepared by mixing, the redox system forms free radicals even at low temperatures.

Examples of known redox systems include combinations of organic peroxides such as benzoyl peroxide or lauroyl peroxide with tertiary aromatic amines such as N,N-dimethyl-p-toluidine or other, structurally related amines as described, for example, in U.S. Pat. No. 3,541,068 or DE 26 58 538 A. A drawback of the peroxide/amine systems is their lack of capacity to effect optimum curing of acidic resin systems, such as are present in bonding materials, for example, in the dental segment.

Other known redox systems are based on derivatives of barbituric and/or thiobarbituric acid. EP 0 480 785 A discloses thiobarbituric or barbituric acid compounds in combination with copper and/or iron halides as polymerization initiators for free-radical polymerization.

DE 42 19 700 A describes an initiator system composed of a thiobarbituric acid derivative, copper salt, and chloride ions for curing 2-hydroxyethyl methacrylate. B. Bredereck et al., Makromol. Chem. 92, 70 (1966) and DE 14 95 520 A describe combinations of barbituric and thiobarbituric acid derivatives with peroxides, copper compounds, and chloride ions (known as a Bredereck system). All of these systems bring about inadequate curing of the compositions in an acidic medium, resulting in high solubilities, low mechanical values, and low color stabilities.

U.S. Pat. No. 5,688,883 describes a system composed of an organic peroxide with a half-life of 10 hours at temperatures of above 75° C., a proton donor (e.g., a barbituric acid derivative), and a metal compound (e.g., a copper compound). This system is capable of polymerizing even acidic compositions. Nevertheless, this system does not produce adhesion between the polymerizing material and the hard tooth substance.

DE 19 757 277 A1 discloses an initiator system composed of a copper salt, a sulfinic acid compound, and a barbituric and/or thiobarbituric acid derivative. By means of this system it is possible to cure acidic dental resin systems and adhesion to the hard tooth substance is attained. The adhesion values, however, range at a comparatively low level.

For the reasons given above it is evident that within the dental sector there is a considerable demand for a redox initiator system which enables filled and unfilled formulations to be cured effectively, preferably in an acidic medium, and which contributes to high levels of adhesion to dentine and enamel.

Surprisingly it has been found that the object according to the invention can be achieved by means of a redox initiator system which comprises the following constituents:

(A) from 14.9 to 50% by weight, preferably from 20 to 45% by weight, of a barbituric acid or thiobarbituric acid and/or of a barbituric or thiobarbituric acid derivative, (B) from 30 to 75% by weight, preferably from 35 to 67.8% by weight, of a peroxodisulfate compound and/or peroxodiphosphate compound, (C) from 10 to 35% by weight, preferably from 12 to 30% by weight, of a sulfinic acid compound, and (D) from 0.1 to 5% by weight, preferably from 0.2 to 4% by weight, of a copper compound.

The terms "include", "contain" or "comprise" introduce a nonexclusive enumeration of features. Similarly, the term "one" is to be understood in the sense of "at least one".

Component (A) comprises a barbituric acid or thiobarbituric acid and/or a barbituric or thiobarbituric acid derivative and/or mixtures thereof of the general structure:

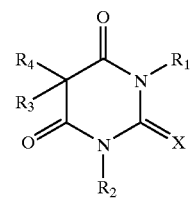

In this structure X=O or S. $R_1$, $R_2$, $R_3$, and $R_4$, which may be identical or different, have the following meanings: hydrogen, alkyl, substituted alkyl, alkenyl, cycloalkyl, substituted cycloalkyl, arylalkyl, aryl or substituted aryl radical. $R_1$, $R_2$, $R_3$, and $R_4$ may also incorporate a halogen radical such as chloro or a hydroxyl, amino or nitro group.

If one of the radicals $R_1$ to $R_4$ is unsubstituted alkyl then this radical can be straight-chain or branched and can contain, for example, from 1 to 18 carbon atoms, preferably from 1 to 10, and in particular from 1 to 6 carbon atoms. Examples of low-molecular alkyl radicals are methyl, ethyl, propyl, isopropyl, n-butyl, t-butyl, isobutyl, n-pentyl, and isoamyl.

If one of the radicals $R_1$ to $R_4$ is a substituted alkyl radical then the alkyl moiety of this radical preferably has the number of carbon atoms indicated above for unsubstituted alkyl. If one of the radicals $R_1$ to $R_4$ is alkoxyalkyl or alkoxycarbonylalkyl then the alkoxy radical contains, for example, from 1 to 5 carbon atoms and is preferably methyl, ethyl, propyl, isopropyl, n-butyl, t-butyl, isobutyl, n-pentyl or isoamyl. If one of the radicals $R_1$ to $R_4$ is haloalkyl then the halo moiety is understood to be fluoro, chloro, bromo or iodo.

If one of the radicals $R_1$ to $R_4$ is alkenyl then preference is given to $C_3$ to $C_5$ alkenyl radicals, especially allyl.

If one of the radicals $R_1$ to $R_4$ is unsubstituted cycloalkyl then preference is given to $C_4$ to $C_7$ cycloalkyl radicals. Cyclopentyl and cyclohexyl are particularly preferred.

If one of the radicals $R_1$ to $R_4$ is substituted cycloalkyl then preference is given to the above-indicated cycloalkyl radicals, with the substituent or substituents on the cycloalkyl radical possibly being, for example, $C_1$ to $C_4$ alkyl such as methyl, ethyl, propyl, n-butyl or isobutyl, fluoro, chloro, bromo, iodo or $C_1$ to $C_4$ alkoxy, especially methoxy.

If one of the radicals $R_1$ to $R_4$ is aryl or aralkyl then preference is given to phenyl and naphthyl as aryl. Particularly preferred arylalkyl radicals are benzyl and phenylethyl.

$R_1$ to $R_4$ may also be substituted aryl radicals if desired. In this case phenyl and naphthyl are preferred and as ring substituents $C_1$ to $C_4$ alkyl, especially methyl, halogen or $C_1$ to $C_4$ alkoxy, especially methoxy.

The following may be mentioned as exemplary representatives of component (A): barbituric acid, thiobarbituric acid, 1,3,5-trimethylbarbituric acid, 1-phenyl-5-benzylbarbituric acid, 1-benzyl-5-phenylbarbituric acid, 1,3-dimethylbarbituric acid, 1,3-dimethyl-5-phenylbarbituric acid, 1-cyclohexyl-5-ethylbarbituric acid, 5-laurylbarbituric acid, 5-butylbarbituric acid, 5-allylbarbituric acid, 5-hydroxy-5-butylbarbituric acid, 5-phenylthiobarbituric acid, 1,3-dimethylthiobarbituric acid, 5,5-dibromobarbituric acid, trichlorobarbituric acid, 5-nitrobarbituric acid, 5-aminobarbituric acid, 5-hydroxybarbituric acid and 5,5-dihydroxybarbituric acid.

The peroxodisulfate compounds and/or peroxodiphosphate compound of component (B) and/or mixtures thereof may be organic and/or inorganic in nature, with preference being given to saltlike compounds, especially water-soluble compounds. Water-soluble in this context means a solubility of at least 4 g substance/100 ml water at 20° C., preferably of at least 10 g substance/100 ml water at 20° C., more preferably of at least 20 g substance/100 ml water at 20° C.

As examples mention may be made of the ammonium, sodium, and potassium peroxodisulfate compounds and/or peroxodiphosphate compounds. Sodium peroxodisulfate is particularly preferred.

It has been found that other peroxo compounds, especially organic peroxo compounds, do not lead to useful results.

Component (C) comprises a sulfinic acid compound and/or mixtures thereof of the general formula $R_1SOO\text{—}R_2$, in which $R_1$ is an alkyl, substituted alkyl, alkenyl, cycloalkyl, substituted cycloalkyl, arylalkyl, aryl or substituted aryl radical and $R_2$=H, metal such as lithium, sodium or potassium or is an alkyl, substituted alkyl, alkenyl, cycloalkyl, substituted cycloalkyl, arylalkyl, aryl or substituted aryl radical.

If one of the radicals $R_1$ or $R_2$ is unsubstituted alkyl then this radical can be straight-chain or branched and can contain, for example, from 1 to 18 carbon atoms, preferably from 1 to 10, and in particular from 1 to 6 carbon atoms. Examples of low-molecular alkyl radicals are methyl, ethyl, propyl, isopropyl, n-butyl, t-butyl, isobutyl, n-pentyl, and isoamyl.

If one of the radicals $R_1$ or $R_2$ is a substituted alkyl radical then the alkyl moiety of this radical preferably has the number of carbon atoms indicated above for unsubstituted alkyl. If one of the radicals $R_1$ or $R_2$ is alkoxyalkyl or alkoxycarbonylalkyl then the alkoxy radical contains, for example, from 1 to 5 carbon atoms and is preferably methyl, ethyl, propyl, isopropyl, n-butyl, t-butyl, isobutyl, n-pentyl or isoamyl. If one of the radicals $R_1$ or $R_2$ is haloalkyl then the halo moiety is understood to be fluoro, chloro, bromo or iodo.

If one of the radicals $R_1$ or $R_2$ is alkenyl then preference is given to $C_3$ to $C_5$ alkenyl radicals, especially allyl.

If one of the radicals $R_1$ or $R_2$ is unsubstituted cycloalkyl then preference is given to $C_4$ to $C_7$ cycloalkyl radicals. Cyclopentyl and cyclohexyl are particularly preferred.

If one of the radicals $R_1$ or $R_2$ is substituted cycloalkyl then preference is given to the above-indicated cycloalkyl radicals, with the substituent or substituents on the cycloalkyl radical possibly being, for example, $C_1$ to $C_4$ alkyl such as methyl, ethyl, propyl, n-butyl or isobutyl, fluoro, chloro, bromo, iodo or $C_1$ to $C_4$ alkoxy, especially methoxy.

If one of the radicals $R_1$ or $R_2$ is aryl or aralkyl then preference is given to phenyl and naphthyl as aryl. Particularly preferred arylalkyl radicals are benzyl and phenylethyl.

$R_1$ or $R_2$ may also be substituted aryl radicals if desired. In this case phenyl and naphthyl are preferred and as ring substituents $C_1$ to $C_4$ alkyl, especially methyl, halogen or $C_1$ to $C_4$ alkoxy, especially methoxy.

As representatives of component (C) exemplary mention may be made of the following: benzenesulfinic acid, sodium benzenesulfinate, sodium benzenesulfinate dihydrate, sodium toluenesulfinate, formamidinesulfinic acid, sodium salt of hydroxymethanesulfinic acid, sodium salt of 2,5-dichlorobenzenesulfinic acid, 3-acetamido-4-methoxybenzenesulfinic acid.

Particularly preferred compounds of component (C) are sodium toluenesulfinate or sodium benzenesulfinate and their hydrates.

The copper compound (D) and/or mixtures thereof possess the general formula $CuX_n$, where X is an organic and/or inorganic anion and n=1 or 2. Examples of suitable copper compounds include copper chloride, copper acetate, copper acetylacetonate, copper naphthenate, copper salicylate or complexes of copper with thiourea or ethylenediaminetetraacetic acid. Copper acetate is particularly preferred.

The fraction of the initiator system of the invention comprising components (A) to (D) in the dental formulations is from 0.5 to 15% by weight and more preferably from 1.0 to 10% by weight. The dental formulations are powder/liquid, paste/paste or liquid/liquid systems. Powder/liquid systems are particularly preferred. For reasons of storage stability the constituents of the initiator system of the invention may be microencapsulated. Methods of microencapsulation are described, for example, in U.S. Pat. No. 5,154,762 and EP 0 588 878 B1.

Immediately after mixing, the dental formulations have a pH of less than 5, preferably of less than 3, and very preferably of less than 1. The pH was determined in accordance with the current version of PH.EUR., section 2.2.3: pH—potentiometric method. The initiator system of the invention allows acidic dental resin systems to be cured within an application-friendly setting time which is situated within the range from 0.5 to 15 min, preferably in the range from 1 to 10 min, measured at 37° C. in accordance with ISO 4049:2000.

The setting time in the sense of the invention begins with mixing of the components. The setting time is followed by the processing time, within which the formulation has cured to such an extent that it can be worked on—for example, can be polished.

The initiator system operates on dry to wet substrates and produces a high level of adhesion of the polymerized material to the hard toothed substance.

The polymerization initiator system of the invention can be used for preparing and applying adhesion-promoting substances, dental fixing compositions and dental filling materials with variable filler content. The polymerization initiator system of the invention is also suitable for curing coating materials and/or adhesives based on ethylenically unsaturated monomers.

The polymerization initiator system of the invention is particularly suitable for curing acidic formulations based on ethylenically unsaturated monomers, (meth)acrylates for example.

The invention is illustrated below with reference to examples without any intention that it should be restricted by them.

EXAMPLE 1

Redox-curing 2 K [2-Component] System (3 Parts Powder/1 Part Liquid)
Powder:
  88.6% by weight of strontium aluminum fluorosilicate glass, silanized with 0.3% by weight of methacryloxypropyltrimethoxysilane
  1.6% by weight of calcium hydroxide
  0.8% by weight of sodium toluenesulfinate
  1.2% by weight of 1,3-dimethyl-5-phenylbarbituric acid
  2.4% by weight of sodium peroxodisulfate
  5.4% by weight of pyrogenic silica (Aerosil OX 50) silanized with 3% by weight of methacryloxypropyltrimethoxysilane
Liquid:
  49.9% by weight of 1,3-glyceryl dimethacrylate phosphate
  20% by weight of propoxylated bisphenol A dimethacrylate
  30% by weight of triethylene glycol dimethacrylate
  0.1% by weight of Cu(II) acetate

EXAMPLE 2

Redox-curing 2 K [2-Component] System (3 Parts Powder/1 Part Liquid)
Powder:
  93.0% by weight of strontium aluminum fluorosilicate glass, silanized with 0.3% by weight of methacryloxypropyltrimethoxysilane
  1.6% by weight of calcium hydroxide
  0.8% by weight of sodium toluenesulfinate
  1.2% by weight of 1,3-dimethyl-5-phenylthiobarbituric acid
  2.4% by weight of sodium peroxodisulfate
  1.0% by weight of pyrogenic silica (Aerosil OX 50), silanized with 3% by weight of methacryloxypropyltrimethoxysilane
Liquid:
  41.9% by weight of hydroxyethyl methacrylate phosphate
  40% by weight of propoxylated bisphenol A dimethacrylate
  18% by weight of triethylene glycol dimethacrylate
  0.1% by weight of Cu(II) acetate

COMPARATIVE EXAMPLE 1

As example 1, but without sodium peroxodisulfate
Powder:
  91.0% by weight of strontium aluminum fluorosilicate glass, silanized with 0.3% by weight of methacryloxypropyltrimethoxysilane
  1.6% by weight of calcium hydroxide
  0.8% by weight of sodium toluenesulfinate
  1.2% by weight of 1,3-dimethyl-5-phenylbarbituric acid
  5.4% by weight of pyrogenic silica (Aerosil OX 50), silanized with 3% by weight of methacryloxypropyltrimethoxysilane
Liquid:
  49.9% by weight of 1,3-glyceryl dimethacrylate phosphate
  20% by weight of propoxylated bisphenol A dimethacrylate
  30% by weight of triethylene glycol dimethacrylate
  0.1% by weight of Cu(II) acetate

COMPARATIVE EXAMPLE 2

As example 1, but without 1,3-dimethyl-5-phenylbarbituric acid
Powder:
  89.8% by weight of strontium aluminum fluorosilicate glass, silanized with 0.3% by weight of methacryloxypropyltrimethoxysilane
  1.6% by weight of calcium hydroxide
  0.8% by weight of sodium toluenesulfinate
  2.4% by weight of sodium peroxodisulfate
  5.4% by weight of pyrogenic silica (Aerosil OX 50), silanized with 3% by weight of methacryloxypropyltrimethoxysilane
Liquid:
  49.9% by weight of 1,3-glyceryl dimethacrylate phosphate
  20% by weight of propoxylated bisphenol A dimethacrylate
  30% by weight of triethylene glycol dimethacrylate
  0.1% by weight of Cu(II) acetate

COMPARATIVE EXAMPLE 3

As example 1, but without sodium toluenesulfinate
Powder:
  89.4% by weight of strontium aluminum fluorosilicate glass, silanized with 0.3% by weight of methacryloxypropyltrimethoxysilane
  1.6% by weight of calcium hydroxide
  1.2% by weight of 1,3-dimethyl-5-phenylbarbituric acid
  2.4% by weight of sodium peroxodisulfate
  5.4% by weight of pyrogenic silica (Aerosil OX 50), silanized with 3% by weight of methacryloxypropyltrimethoxysilane Liquid:
49.9% by weight of 1,3-glyceryl dimethacrylate phosphate
20% by weight of propoxylated bisphenol A dimethacrylate
30% by weight of triethylene glycol dimethacrylate
0.1% by weight of Cu(II) acetate

COMPARATIVE EXAMPLE 4

As example 1, but without Cu(II) acetate
Powder:
88.6% by weight of strontium aluminum fluorosilicate glass, silanized with 0.3% by weight of methacryloxypropyltrimethoxysilane
1.6% by weight of calcium hydroxide
0.8% by weight of sodium toluenesulfinate
1.2% by weight of 1,3-dimethyl-5-phenylbarbituric acid
2.4% by weight of sodium peroxodisulfate
5.4% by weight of pyrogenic silica (Aerosil OX 50), silanized with 3% by weight of methacryloxypropyltrimethoxysilane Liquid:
50% by weight of 1,3-glyceryl dimethacrylate phosphate
20% by weight of propoxylated bisphenol A dimethacrylate
30% by weight of triethylene glycol dimethacrylate Description of the Measurements Carried Out Determination of Adhesion Adhesion tests are carried out using bovine teeth. For each test, five bovine teeth deep-frozen following extraction are thawed, cleaned to remove remaining gum, and the roots are separated by sawing with a diamond saw. The remaining pulp is removed using a pulp needle and the teeth are then washed with mains water. Planar dentine and enamel is obtained by labial sanding of the teeth on a water-cooled diamond sanding disk. The teeth are then embedded in silicone in such a way that the sanded surface, which is kept well moist, points upward and is subsequently worked on wet with a fine silicon carbide sandpaper. Subsequently each tooth has stuck to it a small wax plate which has a circular cutout of 6 mm in diameter (test area). This test area is filled in planar fashion with the material under test, after relative drying, and is cured for 1 h at 36° C. and 100% relative humidity. After curing, the small wax plate is removed, a screw is adhered to the material under test, at right angles to the tooth surface, and after storage of one day at 36° C. and 100% relative humidity the adhesion is measured in a takeoff test on a Zwick UPM with a takeoff rate of 1 mm/min.

Determination of Flexural Strength (3-Point Bending Test to EN ISO 4049:2000)

The results of the flexural strength and adhesion measurements are compiled in table 1.

TABLE 1

| Material | Flexural strength [MPa] | Adhesion to dentine [MPa] | Adhesion to enamel [MPa] |
| --- | --- | --- | --- |
| Example 1 | 58 | 4.1 | 4.4 |
| Example 2 | 54 | 4.7 | 5.1 |
| Comparative example 1 | 56 | 0.0 | 0.0 |
| Comparative example 2 | 9 | 0.0 | 0.0 |
| Comparative example 3 | Not measurable | Not measurable | Not measurable |

TABLE 1-continued

| Material | Flexural strength [MPa] | Adhesion to dentine [MPa] | Adhesion to enamel [MPa] |
| --- | --- | --- | --- |
| Comparative example 4 | Not measurable | Not measurable | Not measurable |

In contrast to the inventive examples 1 and 2, comparative example 1 (without sodium peroxodisulfate) shows no adhesion to the hard toothed substance. Omission of other initiator constituents such as the barbituric acid (derivative) or the sulfinate compound or copper compound has the consequence that no adhesion is achieved and/or that the material is cured incompletely if at all.

Adhesion to Dry and Wet Dentine:

Description of the Measurements Conducted:

The measurements took place on the 2-component system of example 1 as described under "Determination of adhesion". Instead of the relative drying, however, in one case the dentine was blown dry completely under a stream of air and in the other case a film of water was left on the dentine. The results are evident from table 2.

TABLE 2

| Surface | Adhesion [MPa] |
| --- | --- |
| Relatively dried dentine | 4.1 |
| Dried dentine | 4.0 |
| Water film on the dentine | 3.6 |

The results set out in table 2 show that the system of the invention is very tolerant toward the pretreatment of the tooth, since very good adhesions are achieved even in extreme cases.

What is claimed is:

1. A redox initiator system which comprises the following constituents:
   (A) from 14.9 to 50% by weight of a barbituric acid or thiobarbituric acid and/or of a barbituric or thiobarbituric acid derivative,
   (B) from 30 to 75% by weight of a peroxodisulfate compound and/or peroxodiphosphate compound,
   (C) from 10 to 35% by weight of a sulfinic acid compound, and
   (D) from 0.1 to 5% by weight of a copper compound.

2. The redox initiator system of claim 1, wherein component (A) has the following structure:

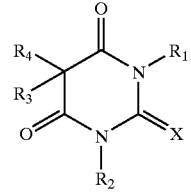

where X=O or S;
   $R_1$, $R_2$, $R_3$, and $R_4$, which may be identical or different, are hydrogen, alkyl, substituted alkyl, alkenyl, cycloalkyl, substituted cycloalkyl, arylalkyl, aryl or substituted aryl radical, a halogen radical such as chloro or a hydroxyl, amino or nitro group.

3. The redox initiator system of claim 1, wherein component (B) has a water-solubility of more than 4 g/100 ml water at 20° C.

4. The redox initiator system of claim 1, wherein component (B) is selected from the group consisting of ammonium peroxodisulfate, sodium peroxodisulfate, and combinations thereof.

5. The redox initiator system of claim 1, wherein component (C) comprises a sulfinic acid compound of the general formula $R_1SOO-R_2$, wherein $R_1$=alkyl, substituted alkyl, alkenyl, cycloalkyl, substituted cycloalkyl, arylalkyl, aryl or substituted aryl radical and $R_2$=H, metal or alkyl, substituted alkyl, alkenyl, cycloalkyl, substituted cycloalkyl, arylalkyl, aryl or substituted aryl radical.

6. The redox initiator system of claim 5, wherein component (C) is selected from the group consisting of sodium benzenesulfinate, sodium toluenesulfinate, hydrates thereof, and combinations thereof.

7. The redox initiator system of claim 1, wherein component (D) is selected from the group consisting of copper chloride, copper acetate, copper acetylacetonate, copper naphtheneate, copper salicylate, complexes of copper with thiourea, complexes of copper with ethylenediaminetetraacetic acid, and combinations thereof.

8. The redox initiator system of claim 1 as a constituent of a free-radically polymerizable composition having pH values of less than 5 after mixing with the redox initiator system.

9. The redox initiator system of claim 8, wherein the composition comprises acid-functional (meth)acrylates.

10. The redox initiator system of claim 1 as a constituent of dental formulations, adhesives or coating materials.

11. The redox initiator system of claim 1 for curing free-radically polymerizable, acidic formulations.

* * * * *